United States Patent [19]

Smutny et al.

[11] 4,229,380

[45] Oct. 21, 1980

[54] PREPARATION OF 3-PHENOXYBENZALDEHYDE

[75] Inventors: Edgar J. Smutny; Thomas H. Colby, both of Houston, Tex.

[73] Assignee: Shell Oil Company, Houston, Tex.

[21] Appl. No.: 925,011

[22] Filed: Jul. 17, 1978

[51] Int. Cl.³ .................... C07C 45/42; C07C 45/43
[52] U.S. Cl. .................................................. 568/435
[58] Field of Search ................................... 260/600 R

[56] References Cited

U.S. PATENT DOCUMENTS

| | | | |
|---|---|---|---|
| 4,085,147 | 4/1978 | Rosinger et al. | 260/600 R |
| 4,108,904 | 8/1978 | Brown et al. | 260/600 R |

OTHER PUBLICATIONS

Hougen & Watson, Chemical Process Principles, Part III, Kinetics & Catalysis (1947) pp. 883–885.

*Primary Examiner*—Bernard Helfin

[57] ABSTRACT

3-Phenoxybenzaldehyde is prepared by adding, at a relatively low temperature, a mixture of a 3-phenoxybenzyl halide and a 3-phenoxybenzal halide to a mixture of hexamethylenetetramine, acetic acid and water, the amounts of the water and acid bearing certain relationships to the amount of the mixture of halides, then heating the resulting mixture to a specified temperature level and maintaining it at that level for a specified period of time.

2 Claims, No Drawings

PREPARATION OF 3-PHENOXYBENZALDEHYDE

BACKGROUND OF THE INVENTION

As is disclosed in Belgian Pat. No. 851,900, 3-phenoxybenzaldehyde is of interest as a precursor for the preparation of insecticidal esters of certain cyclopropanecarboxylic acids. Netherlands patent application No. 7701128 discloses a process for preparing 3-phenoxybenzaldehyde by treating a mixture of a 3-phenoxybenzyl halide and 3-phenoxybenzal halide with hexamethylenetetramine in the presence of acetic acid and water.

DESCRIPTION OF THE INVENTION

For the sake of brevity, hereinafter, hexamethylenetetramine will be denoted by its common abbreviation, HMTA.

It has been found that 3-phenoxybenzaldehyde can be prepared more efficiently by the general process of the Netherlands application—to give a higher yield of the aldehyde, with less undesirable by-products—by first mixing the HMTA, the acetic acid and the water, then adding the benzyl/benzal halide mixture thereto, at a temperature below about 60° C., then heating the resulting mixture at a controlled rate to a temperature of from about 105° C. to about 120° C., and holding it at that temperature for a period of about 3.0 to about 4.5 hours, using particular amounts of water and acetic acid relative to the amount of the halide mixture.

DESCRIPTION OF THE PREFERRED EMBODIMENTS

The starting material in the process of this invention is a mixture of a 3-phenoxybenzyl halide and a 3-phenoxybenzal halide wherein the halogen is bromine or chlorine, the bromides being preferred. The Netherlands application discloses a method for preparing such mixtures. However, a method for preparing mixtures of such bromides that are particularly suited to the process of this invention is disclosed in application Ser. No. 856,702, filed on Dec. 2, 1977.

HMTA per se can be used, or equivalent amounts of ammonia and formaldehyde—i.e., 4 moles of ammonia+6 moles of formaldehyde=1 mole of HMTA—can be used. Where ammonia and formaldehyde are used (ordinarily as gaseous ammonia and formalin solution), they can be added to the mixture of water and acetic acid, or they can be prereacted to form HMTA in the reactor, before the water and acetic acid are added. In both cases, the amount of water introduced into the formalin solution must be taken into account, as must also the heat of reaction of the ammonia and the formaldehyde.

It has been found that the amount of HMTA to be used is related to the amount of the benzyl halide, and to the amount of the benzyl/benzal halide mixture, used. Thus, the conversion of the halides to 3-phenoxybenzaldehyde tends to fall off unduly when less than about moles of HMTA is used per mole of the benzyl halide, with best results being obtained when womewhat more than that minimum—for example, 10-15 percent more—is used. Further, at least one mole of HMTA per mole of the benzyl/benzal halide mixture is required, and again it may be found desirable to use somewhat more than that minimum (i.e., 10-15 percent).

Essential to the significant improvement in the yield of the aldehyde and reduction in the formation of by-products provided by the process of the invention is the use of particular amounts of water and acetic acid, relative to the amount of the benzyl/benzal halide mixture that is used. Thus, at least about 5, but not more than about 16 moles of water should be used per mole (i.e., from about 85 to about 290 pounds of water per pound mole) of the halide mixture, with best results being attained when from about 5.8 to about 11 moles of water are used per mole (about 105 to about 190 pounds of water per pound mole) of the halide mixture. A very convenient source of both the water and the HMTA is the commercially available saturated solution of HMTA in water; it contains 55 percent by weight of water, and this supplies about 10.7 moles of water per mole (192 pounds of water per pound mole) of the halide mixture when about a 10% excess of the HMTA is used per mole of the halide mixture (it supplies about 9.6 or about 171 pounds of water per pound mole of the halide mixture when the stoichiometric amount of HMTA is used). This amount of water, relative to the halide mixture, appears to provide maximum yield of the aldehyde product, with minimum formation of by-products. However, when operating on a large scale, use of the saturated solution of HMTA can raise problems—as when it is chilled and solid HMTA precipitates, causing handling difficulties. Therefore, it may be found desirable to dilute the saturated solution slightly—for example, to provide 60% by weight of water. This supplies about 13 moles (about 235 pounds) of water per mole of the halide mixture (10% excess HMTA) or about 11.7 moles (about 210 pounds) of water per mole of the halide mixture (no excess HMTA). This additional amount of water tends to reduce slightly the yield of aldehyde, with slight rise in the formation of by-products.

Glacial acetic acid is suitable as the source of the acetic acid, or a solution of acetic acid in water can be used, providing that the amount of water therein is taken into account. Glacial acetic acid is preferred.

At least about 3.5 moles of acetic acid is used per mole of the benzyl/benzal halide mixture. Optimum results appear to be attained when about 4 moles of acetic acid per mole of the halide mixture is used. Use of larger amounts of acetic acid does not significantly improve the results, and is undesirable, in that it unnecessarily increases the amount of acetic acid that must be stored and handled.

The process of the invention requires that the four essential materials be mixed in a particular sequence, at a relatively low temperature, and the resulting mixture heated to a higher temperature at a controlled rate, and holding it at that temperature for a certain period of time.

The ingredients should be mixed at as low a temperature as is practically feasible, since it appears that the efficiency of the process increases with decrease in the mixing temperature. This means, on a large-scale basis, ambient temperature, or at most the temperature provided by cooling water—i.e., temperatures of the order of about 10°-25° C. However, for practical reasons, having to do with removal of the heat of reaction between the HMTA and the acetic acid, it may be desirable to conduct the mixing at a somewhat higher temperature, but this must not exceed about 60° C., in order to attain the improved results.

The HMTA, acetic acid and water are fixed mixed, then the benzyl/benzal halide is added thereto. In the preferred practice the HMTA is supplied as an aqueous solution, which is directly mixed with the acetic acid. Since the acid reacts exothermically with the HMTA, it is necessary to remove sufficient of the heat of reaction to attain the necessary low mixing temperature before the halide mixture is added.

The benzyl/benzal halide mixture then is added slowly to the thoroughly stirred mixture and the stirred mixture is slowly (usually over a period of 30-60 minutes, preferably about 40 minutes) heated to a temperature of from about 105° C. to about 120° C. and held within that temperature range for a period of about 3 hours to about 4.5 hours. In most cases, it will be found convenient to reflux the reaction mixture, this providing a temperature of from about 110° C. to about 120° C., depending upon the particular proportions of the ingredients used, and on the autonomic pressure in the reaction system.

The process is conveniently conducted at essentially atmospheric pressure or slightly above—i.e., at the autonomic pressure of the reactor system.

The aldehyde product can be recovered and isolated by cooling the final crude reaction mixture, adding an essentially water-immisible solvent for the aldehyde (toluene is suitable), separating the aqueous phase from the organic phase and removing the organic solvent under reduced pressure.

Conduct of the process of the invention in particular instances is described in the following examples. In these examples, the reactions described were conducted in a 7.5 gallon cylindrical vessel with a hemispheric bottom, equipped with a turbine stirrer and baffles. In each case, a 45 percent by weight solution of HMTA in water was used. The HMTA solution was mixed with glacial acetic acid and the mixture was cooled to the indicated temperature, then the mixture of 3-phenoxybenzyl bromide and 3-phenoxybenzal bromide was added. The mixture then was heated and refluxed for the indicated time, then cooled and extracted with toluene. The mixture of 3-phenoxybenzyl bromide and 3-phenoxybenzal bromide was prepared by the method disclosed in application Ser. No. 856,702. The results are reported in Table I.

TABLE I

|  | Examples | |
| --- | --- | --- |
|  | 1 | 2 |
| Charge, moles |  |  |
| Water | 200.75 | 200.75 |
| HMTA | 21.12 | 21.12 |
| Acetic acid | 84.46 | 84.46 |
| 3-phenoxybenzyl bromide | 12.02 | 12.02 |
| 3-phenoxybenzal bromide | 7.17 | 7.17 |
| Addition temperature, °C. | 35 | 50 |
| Addition time, min. | 30 | 30 |
| Heat up time, min. | 60 | 60 |
| Reflux temperature °C. | 108-112 | 108-112 |
| Reflux time, hours | 4 | 4 |
| Yield of 3-phenoxybenz aldehyde, mole % | 89.5 | 87.7 |

Data obtained from these, and other similar experiments, established the essential features of the invention that have already been described herein, with respect to:

(1) the need for mixing the HMTA, water and acetic acid and then adding the benzyl/benzal bromide mixture thereto;

(2) the need for mixing the HMTA, acetic acid, water, and benzyl/benzal bromide mixture at a temperature below about 60° C., then slowly heating the mixture to a temperature of about 105°-120° C. and holding it at that temperature for about 3-4.5 hours;

(3) the need for using particular amounts of water and acetic acid, relative to the amount of the benzyl/benzal bromide mixture used.

We claim:

1. A process for preparing 3-phenoxybenzaldehyde, which comprises adding a mixture of a 3-phenoxybenzyl halide and a 3-phenoxybenzal halide to a mixture of hexamethylenetetramine, water and acetic acid, at a temperature below about 60° C., then heating the resulting mixture over a period of about 30 to 60 minutes to a temperature of about 105° to about 120° C., and maintaining the mixture at that level for a period of from about 3.0 to about 4.5 hours, and separating 3-phenoxybenzaldehyde from the resulting mixture, the amount of water used being from about 5 to about 16 moles per mole of the mixture of halides, the amount of acetic acid used being at least about 3.5 moles per mole of the mixture of halides and the amount of hexamethylenetetramine used being at least 1.7 moles per mole of the 3-phenoxybenzyl halide.

2. A process according to claim 1 wherein the halogen in the halides is bromine.

* * * * *